United States Patent
Slimestad

(10) Patent No.: US 6,967,032 B2
(45) Date of Patent: Nov. 22, 2005

(54) PRODUCT

(75) Inventor: Rune Slimestad, Sandnes (NO)

(73) Assignee: Medpalett Pharmaceuticals AS, Sandnes (NO)

( * ) Notice: Subject to any disclaimer, the term of this patent is extended or adjusted under 35 U.S.C. 154(b) by 91 days.

(21) Appl. No.: 10/145,510

(22) Filed: May 15, 2002

(65) Prior Publication Data

US 2003/0091660 A1    May 15, 2003

(30) Foreign Application Priority Data

Nov. 9, 2001    (GB) .................................. 0127032

(51) Int. Cl.⁷ ........................... A61K 35/78; A61K 9/48

(52) U.S. Cl. ....................... 424/732; 424/451; 424/463

(58) Field of Search ................................ 424/732, 451, 424/463; 514/27; 510/443; 436/18

(56) References Cited

U.S. PATENT DOCUMENTS

| | | | |
|---|---|---|---|
| 4,320,009 A | * | 3/1982 | Hilton et al. |
| 6,238,673 B1 | * | 5/2001 | Howard ...................... 424/766 |
| 6,635,490 B1 | * | 10/2003 | Fu et al. |
| 2005/0037095 A1 | | 2/2005 | Bailey et al. |
| 2005/0037130 A1 | | 2/2005 | Nair |

FOREIGN PATENT DOCUMENTS

| | | | | |
|---|---|---|---|---|
| EP | 0 412 300 A3 | | 7/1990 | |
| EP | 0 573 777 A1 | | 5/1993 | |
| JP | 62077328 A | * | 4/1987 | .......... A61K 35/78 |
| WO | WO 84/03216 | | 8/1984 | |
| WO | WO 00/33667 | | 6/2000 | |
| WO | WO 02/17945 | | 3/2002 | |

\* cited by examiner

*Primary Examiner*—Michele Flood
(74) *Attorney, Agent, or Firm*—Sughrue Mion, PLLC

(57) ABSTRACT

An orally ingestible composition comprising a coated spray-dried material comprising at least four anthocyanins, at least one of which is a monosaccharide and at least one of which is a disaccharide and a process for its production.

10 Claims, No Drawings

PRODUCT

The present invention relates to a nutritional supplement (nutraceutical) comprising a mixture of at least four anthocyanins, at least one of which is a disaccharide and at least one of which is a monosaccharide, its preparation and its use.

Anthocyanins are glycosides of flavylium salts. Each anthocyanin thus comprises three component parts: the hydroxylated core (the aglycone); the saccharide unit; and the counterion. Anthocyanins are naturally occurring pigments present in many flowers and fruit and individual anthocyanins are available commercially as the chloride salts, e.g. from Polyphenols Laboratories AS, Sandnes, Norway.

As individual compounds, anthocyanins have been proposed for use as antioxidants (e.g. as free radical scavengers) for treatment of the vascular system.

We have found that the beneficial effects of individual anthocyanins are enhanced if instead of an individual anthocyanin, a combination of different anthocyanins is administered orally, in particular a combination comprising both mono and disaccharide anthocyanins. It is thought that the synergistic effect arises at least in part from the different solubilities and different uptake profiles of the different anthocyanins.

Thus viewed from one aspect the invention provides an orally ingestible composition, e.g. a nutritional supplement, comprising a coated spray-dried material comprising at least four anthocyanins, at least one of which is a monosaccharide and at least one of which is a disaccharide.

The composition of the invention preferably contains at least three monosaccharide anthocyanins. Moreover the composition preferably contains at least one monosaccharide anthocyanin in which the saccharide is arabinose.

The composition preferably contains at least one disaccharide anthocyanin in which the disaccharide is rutinose (i.e. 6-rhamnosyl-glucose).

Moreover the composition of the invention preferably contains anthocyanins with at least two different aglycones, more preferably at least four.

Especially preferably the composition contains anthocyanins in which the aglycone units are cyanidin, peonidin, delphinidin, petunidin, malvidin and optionally also pelargonidin.

In one preferred embodiment, the composition also contains at least one trisaccharide anthocyanin.

Example of anthocyanins suitable for the compositions of the invention include: cyanidin-3-O-β-glucoside; cyanidin-3-O-β-galactoside; cyanidin-3-O-α-arabinoside; cyanidin-3-O-β-xyloside; cyanidin-3-O-(6"-O-β-rhamnosyl-β-glucoside); cyanidin-3-O-(2"-O-β-glucosyl-β-galactoside); cyanidin-3-O-(2"-O-β-glucosyl-β-glucoside); cyanidin-3-O-(2"-O-β-xylosyl-β-glucoside); cyanidin-3-O-(2"-O-β-xylosyl-β-galactoside); cyanidin-3,5-di-O-β-glucoside; cyanidin-3-O-β-galactoside-5-O-β-glucoside; cyanidin-3-O-α-arabinoside-5-O-β-glucoside; cyanidin-3-O-(2"-O-β-xylosyl-β-glucoside)-5-O-β-glucoside; cyanidin-3-O-(2"-O-β-xylosyl-6"-O-β-glucosyl-β-galactoside); pelargonidin-3-O-β-glucoside; pelargonidin-3-O-(6"-O-α-rhamnosyl-β-glucoside); pelargonidin-3,5-di-O-β-glucoside; peonidin-3-O-β-glucoside; peonidin-3-O-α-arabinoside; peonidin-3,5-di-O-β-glucoside; delphinidin-3-O-β-glucoside; delphinidin-3-O-(6"-O-α-rhamnosyl-β-glucoside); delphinidin-3-O-(2"-O-β-xylosyl-β-glucoside); petunidin-3-O-β-glucoside; malvidin-3-O-β-glucoside; malvidin-3,5-di-O-β-glucoside; and malvidin-3-O-α-arabinoside-5-O-β-glucoside.

If desired, one or more hydroxy groups, especially on the saccharide unit, in the anthocyanins may be acylated, e.g. carrying a $C_{1-12}$, more especially a $C_{3-9}$ saturated or unsaturated acyl group, for example a mono-or dicarboxylic acid residue, e.g. a malonyl, p-coumaryl or feruloylyl group. Thus for example such acylated compounds include cyanidin-3-O-(6"-O-(E-p-coumaryl)-2"-O-β-xylosyl-β-glucoside); cyanidin-3-O-(6"-O-(E-p-coumaryl)-2"-O-β-xylosyl-β-glucoside)-5-O-β-glucoside; cyanidin-3-O-(2"-O-β-xylosyl-6"-O-(E-feruloyl-β-glucosyl)-β-galactoside); cyanidin-3-O-(2"-O-β-xylosyl -6"-O-[E-coumaryl-β-glucosyl]β-galactoside); and petunidin-3-O-(6"-O-(4"'-O-E-coumaryl)-α-rhamnosyl-β-glucoside)-5-O-β-glucoside.

The counterion in the anthocyanins in the compositions of the invention may be any physiologically tolerable counteranions, e.g. chloride, succinate, fumarate, malate, maleate, citrate, etc. Preferably however the counterion is a fruit acid anion, in particular citrate, as this results in the compositions of the invention having a particularly pleasant taste.

Particularly suitable sources for the anthocyanins for the compositions of the invention are fruits such as cherries, bilberries, blueberries, blackcurrants, redcurrants, grapes, cranberries, strawberries, and apples and vegetables such as red cabbage. Bilberries, in particular *Vaccinium myrtillus*, and blackcurrants, in particular *Ribes nigrum*, are especially suitable. The berries of *V. myrtillus* contain fifteen monosaccharide anthocyanins, namely the aglycone:saccharide combinations of cyanidin, peonidin, delphinidin, petunidin and malvidin and glucose, galactose and arabinose. The currants of *R. nigrum* contain four anthocyanins, namely the 3-glucosides and 3-rutinosides of cyanidin and delphinidin.

The disaccharide anthocyanins are more water-soluble than the monosaccharides; moreover cyanidin and delphinidin anthocyanins are amongst the most water-soluble anthocyanins.

Besides the anthocyanins, the compositions of the invention may desirably contain further beneficial or inactive ingredients, e.g. vitamins (in particular vitamin C), flavones, isoflavones, anticoagulants (e.g. maltodextrin, silica, etc.), desiccants, etc. Desirably however the anthocyanins constitute at least 50% by weight of the compositions, excluding the coating material.

While the combination of different anthocyanins is central to the present invention, it also represents a problem to produce due to their different physicochemical properties. The commercially available individual anthocyanins do not readily mix to form a free-flowing powder such as would be particularly suitable for tableting or filling into capsules. Normal fruit extracts containing anthocyanins cannot be spray-dried to a free-flowing powder yielding instead a sticky mess. We have found that for spray drying to be successful, the anthocyanin solution must be freed of free sugars and acids, and plant-derived lipids and macromolecules, in particular lectins.

Thus viewed from a further aspect the invention provides a process for the production of an anthocyanin-containing product, said process comprising: loading an aqueous anthocyanin solution (e.g. a liquid plant extract) onto a cation exchange resin; flushing the resin with water; applying an acidic alkanol eluant to said resin until anthocyanin begins to elute therefrom whereafter applying a non-acidic alkanol eluant to said resin; collecting anthocyanin-containing eluate from said resin; evaporating off alkanol from said eluate; adding water and if necessary an anticoagulant to the eluant to produce an aqueous anthocyanin solution, preferably a solution containing at least two anthocyanins; spray-drying said solution; and optionally coating the spray dried product (optionally after mixing with further physiologically tolerable components, e.g. vitamin C, further anthocyanins, etc. and/or after tableting).

The spray-drying is preferably effected using by spraying into an inert atmosphere, e.g. a nitrogen atmosphere, with inlet temperatures of 130 to 160° C. and flow rates of 5 to 12 L/hour. If the spray-dried product is sticky, then increasing flow rate and inlet temperature and/or increasing anticoagulant content and/or increasing atomiser rotation rate will result in a non-sticky product. The optimum temperature, flow-rate, etc. can be determined in this way for each separate anthocyanin source. The anthocyanin solution to be spray-dried desirably is an aqueous solution containing anthocyanins at 5 to 15% wt, more preferably 8 to 12% wt, dry solids basis.

The compositions of the invention are coated. This is important due to the hygroscopic nature of the anthocyanins. Coating may be by conventional coating techniques following tableting of the spray dried product; alternatively, and preferably, coating is achieved by filling the spray dried product into capsules. While conventional gelatin capsules may be used, it is preferred to use cellulose capsules, such as Vcaps from Capsugel SA, Belgium.

The coated compositions of the invention preferably contain 50 to 250 mg anthocyanin per dose unit (e.g. capsule), more preferably 70 to 160 mg.

The dosage for a human consumer is preferably 50 to 250 mg anthocyanin per day, e.g. one or two 75 mg anthocyanin capsules per day. This corresponds approximately to the anthocyanin content of one or two cups full of fresh berries.

As mentioned above, the compositions preferably also contain vitamin C, e.g. 10 to 1000, preferably 20 to 200, mg per gram anthocyanin.

Besides anthocyanins, the compositions of the invention will generally also contain a anticoagulant, e.g. maltodextrin, lactose or silica, added to the anthocyanin solution to be spray dried to prevent coagulation in the spray drying process. Typically the anticoagulant will be present at 0.3 to 0.8 g, especially about 0.5 g, per gram anthocyanin.

Where anthocyanins from more than one plant source are to be included in the compositions of the invention, they are preferably mixed after spray-drying. Thus, for example, the compositions of the invention preferably contain anthocyanins from *V. myrtillus* and *R. nigrum* mixed after spray-drying, preferably in a weight ratio of 0.5:1 to 1:0.5, especially about 1:1.

As mentioned above, the individual anthocyanins available commercially and used in research and as the active components of medicaments are not readily formulated into the sorts of free-flowing powders that are particularly suitable for tableting or capsule filling. This is inconvenient for handling and formulation, and the spray drying procedure of the invention may readily be used to transform such compounds into an easily handleable free-flowing powder. This forms a further aspect of the invention. Viewed from this aspect the invention provides an anthocyanin composition consisting essentially of a spray dried mixture of one or two anthocyanins and an anticoagulant, and pharmaceutical compositions, preferably coated compositions, comprising said anthocyanin composition optionally together with at least one physiologically tolerable carrier or excipient.

The invention will now be described further with reference to the following non-limiting Examples.

EXAMPLE 1

Anthocyanin Extraction

As raw material is used the cakes of fruit skin produced as the waste product in fruit juice pressing from *V. myrtillus* and *R. nigrum*. Fruit juice producers generally add lectinases to the fruit before pressing to release anthocyanins into the juice produced; however the cake still contains a high anthocyanin content.

200L methanol, with 0.1% wt. HCl content, is added to 120 kg fruit skin cake. The mixture is allowed to stand for 24 hours at ambient temperature (20–25° C.) whereafter the methanol is drained off. 150 L methanol (0.1% HCl) is then added to the fruit skin. The mixture is allowed to stand for 24 hours at ambient temperature (20–25° C.) whereafter the methanol is drained off. A further 150 L methanol (0.1% HCl) is then added to the fruit skin. The mixture is allowed to stand for 24 hours at ambient temperature (20–25° C.) whereafter the methanol is drained off. The methanolic solutions are combined and concentrated to 30% on a nanofilter membrane (e.g. such as are available from Osmonics) with an exclusion limit of 300 D.

If desired, ethanol may be used in place of methanol and a lectinase may be added to the methanol for the soaking step.

The concentrated methanolic solutions are further concentrated to 5% wt. dry solids content on a rotary evaporator.

Ion-exchanged water (5 to 10 L) is added to the concentrate to produce an essentially aqueous solution which is then mixed thoroughly in about 1:1 volume ratio with ethyl acetate. The phases are separated and traces of ethyl acetate are evaporated from the anthocyanin containing aqueous phase.

The aqueous phase is then loaded onto an ion exchange column (e.g. Amberlite XAD7) which is flushed with ion exchanged water.

Methanol, 0.25% wt. citric acid, is then added to the column until anthocyanins begin to appear in the eluate whereafter elution is continued with pure methanol. In this way the eluate collected is essentially free of free citric acid.

The eluate is evaporated down on a rotary evaporator to a dry solids content of 10% wt. Water is added and the remaining methanol is evaporated off to a dry solids content of 10% wt. Maltodextrin is then added to bring the dry solids content up to 15% wt.

EXAMPLE 2

Spray-drying

The aqueous solution produced in Example 1 is spray-dried in a pharmaceutical spray dryer (Type SD-4-R-CC) from Niro A/S, Copenhagen, Denmark in a nitrogen atmosphere, using a rotary atomizer, with an inlet temperature of 130–160° C. and with a flow rate of 5 to 12 L/hour.

The product is a free flowing deep purple powder which should be stored in a dry atmosphere.

EXAMPLE 3

Capsules

The spray-dried products from *V. myrtillus* and *R. nigrum*, produced in Example 2 (with a water content of less than 5% wt.) are mixed in a 1:1 weight ratio and filled into cellulose capsules (V caps) to produce an anthocyanin content per capsule of 75 mg or 150 mg.

The capsules are then packed in blister packs.

What is claimed is:

1. An orally ingestible composition comprising a spray-dried material and a coating, wherein said spray-dried material comprises: cyanidin 3-glucoside, cyanidin galactoside, cyanidin arabinoside, cyanidin 3 rutinoside, peonidin glucoside, peonidin galactoside, peonidin arabinoside, delphinidin 3-glucoside, delphinidin galactoside, delphinidin arabinoside, delphinidin 3-rutinoside, petunidin glucoside, petunidin galactoside, petunidin arabinoside, malvidin glucoside, malvidin galactoside and malvidin arabinoside.

2. The composition as claimed in claim 1, wherein said spray-dried material further comprises an anthocyanin with a pelargonidin aglycone unit.

3. The composition as claimed in claim 1, wherein said spray-dried material further comprises at least one trisaccharide anthocyanin.

4. The composition as claimed in claim 1, wherein said spray-dried material further comprises an anthocyanin selected from the group consisting of cyanidin-3-O-β-xyloside; cyanidin-3-O-(2"-O-β-glucosyl-β-galactoside); cyanidin-3-O-(2"-O-β-glucosyl-β-glucoside); cyanidin-3-O-(2"-O-β-xylosyl-β-glucoside); cyanidin-3-O-(2"-O-β-xylosyl-β-galactoside); cyanidin-3,5-di-O-β-glucoside; cyanidin-3-O-β-galactoside-5-O-β-glucoside; cyanidin-3-O-α-arabinoside-5-O-β-glucoside; cyanidin-3-O-(2"-O-β-xylosyl-β-glucoside)-5-O-β-glucoside; cyanidin-3-O-(2"-O-β-xylosyl-6"-O-β-glucosyl-β-galactoside); pelargonidin-3-O-β-glucoside; pelargonidin-3-O-(6"-O-α-rhamnosyl-β-glucoside); pelargonidin-3,5-di-O-β-glucoside; peonidin-3,5-di-O-β-glucoside; delphinidin-3-O-(2"-O-β-xylosyl-β-glucoside); malvidin-3,5-di-O-β-glucoside; and malvidin-3-O-α-arabinoside-5-O-β-glucoside.

5. The composition as claimed in claim 1, wherein said spray-dried material comprises an anthocyanin in which at least one hydroxyl group is acylated.

6. The composition as claimed in claim 5, wherein said spray-dried material comprises an anthocyanin having an acylated hydroxyl group substituent on a saccharide unit.

7. The composition as claimed in claim 1, wherein said spray-dried material contains anthocyanins from *Vaccinum myrtillus* and *Ribes nigrum* in a weight ratio of 0.5:1 to 1:0.5.

8. The composition as claimed in claim 1 in dosage unit form containing 50 to 250 mg anthocyanin per dose unit.

9. The composition as claimed in claim 1, wherein said anthocyanins constitute at least 50% by weight of the spray-dried material.

10. The composition of claim 1, wherein said coating material is cellulose or gelatin.

* * * * *